United States Patent
Morita et al.

(10) Patent No.: US 8,603,507 B2
(45) Date of Patent: *Dec. 10, 2013

(54) SILICONE OIL EMULSION, METHOD OF PRODUCING SAME, AND SILICONE OIL COMPOSITION

(75) Inventors: Yoshitsugu Morita, Ichihara (JP); Tadashi Takimoto, Ichihara (JP)

(73) Assignee: Dow Corning Toray Co., Ltd., Chiyoda-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/513,805

(22) PCT Filed: Dec. 2, 2010

(86) PCT No.: PCT/JP2010/072073
§ 371 (c)(1),
(2), (4) Date: Aug. 8, 2012

(87) PCT Pub. No.: WO2011/068253
PCT Pub. Date: Jun. 9, 2011

(65) Prior Publication Data
US 2012/0301524 A1   Nov. 29, 2012

(30) Foreign Application Priority Data
Dec. 4, 2009   (JP) ................... 2009-276770

(51) Int. Cl.
*A61K 8/02* (2006.01)
*A61K 8/00* (2006.01)
*A61K 31/695* (2006.01)

(52) U.S. Cl.
USPC .............. 424/401; 424/61; 424/63; 424/64; 424/65; 424/59; 514/63

(58) Field of Classification Search
USPC ............. 424/401, 61, 63, 64, 65, 59; 514/63
See application file for complete search history.

(56) References Cited

U.S. PATENT DOCUMENTS

| | | | |
|---|---|---|---|
| 6,057,386 A | 5/2000 | Morita et al. | |
| 6,238,656 B1 | 5/2001 | Morita et al. | |
| 6,388,005 B1 | 5/2002 | Morita et al. | |
| 6,461,597 B1 | 10/2002 | Morita et al. | |
| 2009/0010866 A1* | 1/2009 | Avery | 424/70.12 |
| 2012/0301525 A1* | 11/2012 | Morita et al. | 424/401 |

FOREIGN PATENT DOCUMENTS

| | | |
|---|---|---|
| EP | 0964023 A2 | 12/1999 |
| EP | 1103574 A1 | 5/2001 |
| JP | 2000-281523 A | 10/2000 |
| JP | 2000-281903 A | 10/2000 |
| JP | 2001-139416 A | 5/2001 |
| JP | 2001-139819 A | 5/2001 |
| WO | WO 2011/068252 A1 | 6/2011 |

OTHER PUBLICATIONS

English language abstract for JP 2000-281523 extracted from the espacenet.com database on Aug. 16, 2012, 24 pages.
English language abstract for JP 2000-281903 extracted from the espacenet.com database on Aug. 16, 2012, 14 pages.
English language abstract for JP 2001-139416 extracted from the espacenet.com database on Aug. 16, 2012, 22 pages.
English language abstract for JP 2001-139819 extracted from the espacenet.com database on Aug. 16, 2012, 14 pages.
International Search Report for Application No. PCT/JP2010/072073 dated Mar. 23, 2011, 3 pages.
International Search Report for Application No. PCT/JP2010/072072 dated Mar. 16, 2011, 3 pages.

* cited by examiner

*Primary Examiner* — Aradhana Sasan
(74) *Attorney, Agent, or Firm* — Howard & Howard Attorneys PLLC

(57) ABSTRACT

To provide a silicone oil emulsion that can improve the properties of cosmetic materials and that contains crosslinked silicone particles in water-dispersed silicone oil droplets; a method of producing this silicone oil emulsion; and a silicone oil composition thereof. This invention is a silicone oil emulsion comprising crosslinked silicone particles having an average particle size of 0.05 to 100 μm in silicone oil droplets that are dispersed in water and that have an average particle size of 0.1 to 500 μm wherein the silicone oil is an alkyl-modified silicone oil that has a silicon-bonded alkyl group having at least 4 carbons and the crosslinked silicone particles preferably have a silicon-bonded alkyl group having at least 4 carbons. Also, a silicone oil composition as provided by removing the water from this silicone oil emulsion.

8 Claims, No Drawings

SILICONE OIL EMULSION, METHOD OF PRODUCING SAME, AND SILICONE OIL COMPOSITION

RELATED APPLICATIONS

This application claims priority to and all the advantages of International Patent Application No. PCT/JP2010/072073, filed on Dec. 2, 2010, which claims priority to Japanese Patent Application No. JP2009-276770, filed on Dec. 4, 2009.

TECHNICAL FIELD

The present invention relates to a silicone oil emulsion and a method of producing this silicone oil emulsion and to a silicone oil composition.

BACKGROUND ART

Silicone oil emulsions comprising crosslinked silicone particles in water-dispersed silicone oil droplets are described in Patent Documents 1 and 2. A dimethylpolysiloxane endblocked by the trimethylsiloxy group at both molecular chain terminals is used as the silicone oil here. In addition, Patent Documents 1 and 2 teach the use of these silicone oil emulsions—or the silicone oil compositions obtained by removing the water from these emulsions—as cosmetic materials.

Various properties have come to be required in recent years from the silicone oil emulsions and silicone oil compositions that are used for cosmetic products. For example, the ability to prevent tangled hair and the ability to impart a smooth and silky feel are required in the case of hair cosmetics, while with skin cosmetics the ability to form a suitably spreadable and lustrous film on the skin is required.
[Patent Document 1] JP 2000-281523 A
[Patent Document 2] JP 2000-281903 A

SUMMARY OF INVENTION

Technical Problems to be Solved

An object of the present invention is to provide a silicone oil emulsion that contains crosslinked silicone particles in alkyl-modified silicone oil droplets that are dispersed in water. Additional objects of the present invention are to provide a method of producing this silicone oil emulsion and to provide a silicone oil composition in which crosslinked silicone particles are uniformly dispersed in an alkyl-modified silicone oil.

Solution to Problems

The present inventors have found that a silicone oil emulsion and a silicone oil composition that satisfy these requirements can be obtained by using an alkyl-modified silicone oil that has an at least $C_4$ alkyl group bonded to silicon and additionally by using a crosslinked silicone particle that has an at least $C_4$ alkyl group bonded to silicon. The silicone oil emulsion of the present invention comprises crosslinked silicone particles having an average particle size of 0.05 to 100 µm in silicone oil droplets that are dispersed in water and that have an average particle size of 0.1 to 500 µm wherein the particle size of the crosslinked silicone particles is less than the particle size of the silicone oil droplets, and is characterized in that the silicone oil is an alkyl-modified silicone oil that has an at least $C_4$ alkyl group bonded to silicon. The crosslinked silicone particle characteristically preferably has an at least $C_4$ alkyl group bonded to silicon.

The production method of the present invention carries out a crosslinking reaction in water on a crosslinkable silicone composition containing a noncrosslinking silicone oil to produce a silicone oil emulsion that contains crosslinked silicone particles having an average particle size of 0.05 to 100 µm in silicone oil droplets that are dispersed in the water and that have an average particle size of 0.1 to 500 µm wherein the particle size of the crosslinked silicone particles is less than the particle size of the silicone oil droplets, and is characterized in that the silicone oil is an alkyl-modified silicone oil that has an at least $C_4$ alkyl group bonded to silicon. The crosslinked silicone particle characteristically preferably has an at least $C_4$ alkyl group bonded to silicon.

The silicone oil composition of the present invention is a silicone oil composition as provided by removing the water from a silicone oil emulsion that contains crosslinked silicone particles having an average particle size of 0.05 to 100 µm in silicone oil droplets that are dispersed in water and that have an average particle size of 0.1 to 500 µm wherein the particle size of the crosslinked silicone particles is less than the particle size of the silicone oil droplets, and is characterized in that the silicone oil is an alkyl-modified silicone oil that has an at least $C_4$ alkyl group bonded to silicon. The crosslinked silicone particle characteristically preferably has an at least $C_4$ alkyl group bonded to silicon.

Advantageous Effects of Invention

A characteristic feature of the silicone oil emulsion of the present invention is that this silicone oil emulsion contains crosslinked silicone particles in alkyl-modified silicone oil droplets that are dispersed in water and it can thereby improve the properties of cosmetic materials. A characteristic feature of the method of the present invention for producing a silicone oil emulsion is that this method can efficiently produce the indicated silicone oil emulsion. A characteristic feature of the silicone oil composition of the present invention is that it can improve the properties of cosmetic materials because the crosslinked silicone particles in the silicone oil composition are uniformly dispersed in an alkyl-modified silicone oil.

BEST MODE FOR CARRYING OUT THE INVENTION

The silicone oil emulsion of the present invention is described in detail first.

The silicone oil emulsion of the present invention contains crosslinked silicone particles in water-dispersed silicone oil droplets and is characterized in that this silicone oil is an alkyl-modified silicone oil that has an at least $C_4$ alkyl group bonded to silicon. This alkyl group in the silicone oil contains at least 4 carbons and preferably contains at least 6 carbons and particularly preferably contains at least 8 carbons. While there is no limitation on the upper limit on the number of carbons in this alkyl group, this alkyl group preferably contains no more than 30 carbons and particularly preferably contains no more than 20 carbons. This alkyl group can be exemplified by butyl, pentyl, hexyl, heptyl, octyl, nonyl, and decyl. The molecular structure of this silicone oil is not limited and can be exemplified by straight chain, branched chain, and cyclic. The silicon-bonded groups in this silicone oil other than the at least $C_4$ alkyl can be exemplified by alkyl groups having not more than 3 carbons, e.g., methyl, ethyl, and propyl; alkenyl groups such as vinyl, allyl, and butenyl; aryl groups such as phenyl, tolyl, and xylyl; halogenated alkyl groups such as 3,3,3-trifluoropropyl; alkoxy groups such as methoxy, ethoxy, and propoxy; and also by the hydrogen atom and the hydroxyl group. Methyl and phenyl are preferred.

There are no particular limitations on the viscosity of this alkyl-modified silicone oil at 25° C., but the viscosity at 25° C. is preferably in the range from 1 to 100,000,000 mPa·s and particularly preferably is in the range from 2 to 10,000,000 mPa·s. This alkyl-modified silicone oil is preferably compatible with the crosslinkable silicone composition that will form the crosslinked silicone particles and also preferably does not participate in the crosslinking reaction that occurs when these crosslinked silicone particles are formed. In specific terms, when this crosslinking reaction is the hydrosilylation reaction, preferably neither alkenyl nor silicon-bonded hydrogen is present in the molecule; when this crosslinking reaction is a condensation reaction, preferably neither silicon-bonded hydrogen nor silicon-bonded alkoxy is present in the molecule.

This alkyl-modified silicone oil can be represented, for example, by the following average formula.

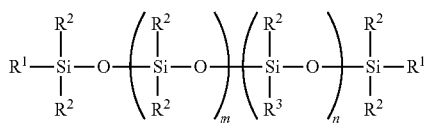

$R^1$ in this formula is an alkyl group having no more than 3 carbons, an alkyl group having at least 4 carbons, an aryl group, or a halogenated alkyl group and can be exemplified by the same groups as provided above. $R^2$ in the formula is an alkyl group having no more than 3 carbons, an aryl group, or a halogenated alkyl group and can be exemplified by the same groups as provided above. $R^3$ in the formula is an alkyl group having at least 4 carbons and can be exemplified by the same groups as provided above. m and n in the formula are each zero or a positive number, wherein when n is zero, at least one of $R^1$ is an alkyl group having at least 4 carbons.

The alkyl-modified silicone oil in the emulsion of this invention is dispersed in droplet form in the water. The average particle size of these droplets is in the range from 0.1 to 500 μm and is preferably in the range from 0.2 to 500 μm, more preferably in the range from 0.5 to 500 μm, and particularly preferably in the range from 0.5 to 200 μm. The reasons for this are as follows: it is quite difficult to prepare an emulsion in which the droplets have an average particle size below the lower limit on the indicated range, while an emulsion in which the upper limit on the indicated range is exceeded has a reduced stability.

The crosslinked silicone particles in the emulsion under consideration also preferably have an at least $C_4$ alkyl group bonded to silicon. This alkyl group preferably contains at least 5 carbons, more preferably at least 6 carbons, and particularly preferably at least 8 carbons. While there is no limitation on the upper limit on the number of carbons in this alkyl group, this alkyl group preferably contains no more than 30 carbons and particularly preferably contains no more than 20 carbons. This alkyl group can be exemplified by butyl, pentyl, hexyl, heptyl, octyl, nonyl, and decyl.

The average particle size of this crosslinked silicone particle is in the range from 0.05 to 100 μm and is preferably in the range from 0.1 to 100 μm and is particularly preferably in the range from 0.1 to 50 μm. When the average particle size of the silicone oil droplets is in the range from 0.2 to 500 μm, the average particle size of the crosslinked silicone particles is preferably in the range from 0.1 to 100 μm and particularly preferably is in the range from 0.1 to 50 μm. When the average particle size of the silicone oil droplets is in the range from 0.5 to 500 μm, the average particle size of the crosslinked silicone particles is preferably in the range from 0.1 to 100 μm and particularly preferably is in the range from 0.1 to 50 μm. When the average particle size of the silicone oil droplets is in the range from 0.5 to 200 μm, the average particle size of the crosslinked silicone particles is preferably in the range from 0.1 to 100 μm and particularly preferably is in the range from 0.1 to 50 μm. The reasons for this are as follows: it is quite difficult to produce crosslinked silicone particles that have an average particle size below the lower limit on the indicated range, while the emulsion has a diminished stability when the crosslinked silicone particles exceed the upper limit on the indicated range. The particle size of the crosslinked silicone particles in the emulsion must of course be smaller than the particle size of the silicone oil droplets. The shape of the crosslinked silicone particles can be exemplified by spherical, spindle shaped, flat, or irregular and is preferably spherical. The properties of the crosslinked silicone particle are preferably elastomeric, e.g., gel-like, rubbery, and so forth.

The crosslinked silicone particles in the emulsion under consideration are provided by the crosslinking of a crosslinkable silicone composition and can be exemplified by the crosslinked silicone particles provided by the crosslinking of a hydrosilylation reaction-crosslinkable silicone composition, the crosslinked silicone particles provided by the crosslinking of a condensation reaction-crosslinkable silicone composition, the crosslinked silicone particles provided by the crosslinking of an organoperoxide-mediated radical reaction-crosslinkable silicone composition, and the crosslinked particles provided by the crosslinking of a radical reaction-crosslinkable silicone composition that is crosslinked by exposure to high-energy radiation. The crosslinked silicone particles are preferably provided by the crosslinking of a hydrosilylation reaction-crosslinkable silicone composition or a condensation reaction-crosslinkable silicone composition.

The method of the present invention for producing the silicone oil emulsion is described in detailed herebelow.

The crosslinkable silicone composition used by the production method of the present invention preferably forms an elastomeric crosslinked product, e.g., a rubbery crosslinked product, a gel crosslinked product, and so forth, by its crosslinking reaction. Such a crosslinkable silicone composition can be exemplified by hydrosilylation reaction-crosslinkable silicone compositions, condensation reaction-crosslinkable silicone compositions, organoperoxide-mediated radical reaction-crosslinkable silicone compositions, and radical reaction-crosslinkable silicone compositions that are crosslinked by exposure to high-energy radiation, wherein hydrosilylation reaction-crosslinkable silicone compositions and condensation reaction-crosslinkable silicone compositions are preferred.

This hydrosilylation reaction-crosslinkable silicone composition can be exemplified by a hydrosilylation reaction-crosslinkable silicone composition that comprises at least (A) an organopolysiloxane that has at least two alkenyl groups in each molecule, (B) an organopolysiloxane that has at least two silicon-bonded hydrogen atoms in each molecule, and (C) a hydrosilylation reaction catalyst.

The alkenyl in component (A) can be exemplified by vinyl, allyl, butenyl, pentenyl, and hexenyl wherein vinyl is particularly preferred. The non-alkenyl silicon-bonded organic groups in component (A) can be exemplified by monovalent hydrocarbyl groups excluding alkenyl groups, e.g., alkyl groups such as methyl, ethyl, propyl, butyl, and so forth; cycloalkyl groups such as cyclopentyl, cyclohexyl, and so forth; aryl groups such as phenyl, tolyl, xylyl, and so forth; aralkyl groups such as benzyl, phenethyl, 3-phenylpropyl, and so forth; and halogenated alkyl groups such as 3-chloropropyl, 3,3,3-trifluoropropyl, and so forth. The molecular structure of component (A) can be exemplified by straight chain, cyclic, network or mesh, and partially branched straight chain, wherein straight chain and partially branched straight chain are preferred for forming elastomeric crosslinked silicone particles. The viscosity of component (A) at 25° C. is not limited but is preferably in the range from 20 to 100,000 mPa·s and particularly preferably is in the range from 20 to 10,000 mPa·s.

The organic groups bonded to silicon in component (B) other than the silicon-bonded hydrogen can be exemplified by the same non-alkenyl monovalent hydrocarbyl groups as provided above. The molecular structure of component (B) can be exemplified by straight chain, cyclic, network or mesh, and partially branched straight chain. The viscosity of component (B) at 25° C. is not limited but is preferably in the range from 1 to 10,000 mPa·s. Component (B) is incorporated in the composition under consideration in an amount sufficient to bring about the crosslinking of this composition, and in specific terms is preferably incorporated in the range from 0.3 to 200 weight parts per 100 weight parts component (A).

Component (C) is a hydrosilylation reaction catalyst for the purpose of promoting or accelerating the crosslinking reaction in the composition under consideration, and platinum-type catalysts are particularly preferred. This platinum-type catalyst can be exemplified by chloroplatinic acid, alcohol solutions of chloroplatinic acid, platinum/olefin complexes, platinum/alkenylsiloxane complexes, platinum black, and silica-supported platinum. Component (C) is incorporated in the composition under consideration in an amount sufficient to promote or accelerate the crosslinking reaction in the composition. In specific terms, and considering the use of a platinum-type catalyst as component (C), component (C) is preferably incorporated in an amount that provides from $1 \times 10^{-7}$ to $1 \times 10^{-3}$ weight part platinum metal in component (C) per 100 weight parts for the total of components (A) and (B).

In order to introduce an at least $C_4$ alkyl group onto the silicon in the crosslinked silicone particles in the emulsion under consideration, the hydrosilylation reaction-crosslinkable silicone composition comprising components (A), (B), and (C) preferably also incorporates (D) an olefin having at least 4 carbons.

The component (D) olefin has at least 4 carbons and preferably has at least 5 carbons, more preferably at least 6 carbons, and particularly preferably at least 8 carbons. The upper limit on the number of carbons in component (D) is not limited, but component (D) preferably contains no more than 30 carbons and particularly preferably contains no more than 20 carbons. Component (D) can be exemplified by butene, pentene, hexene, heptene, octene, decene, undecene, dodecene, tridecene, and tetradecene. Component (D) is preferably an α-olefin, in which the carbon-carbon double bond is present at the end of the molecular chain. Component (D) is incorporated in the composition under consideration in an amount sufficient to introduce an at least $C_4$ alkyl group into the crosslinked silicone particles yielded by the crosslinking of this composition, but its quantity of incorporation is not otherwise limited. In specific terms, it is preferably incorporated at from 0.05 to 50 weight parts per 100 weight parts component (A) and particularly preferably is incorporated at from 0.05 to 15 weight parts per 100 weight parts component (A).

In the execution of the crosslinking of the composition under consideration while it is dispersed in water, component (C) may be incorporated in the composition in advance, or the crosslinkable silicone composition exclusive of component (C) may be dispersed in the water and the composition may be crosslinked by the subsequent introduction of component (C) into the water. The use is preferred in the latter case of a water-based dispersion in which component (C) is dispersed into an average particle size of not more than 1 μm.

The condensation reaction-crosslinkable silicone composition can be exemplified by a condensation reaction-crosslinkable silicone composition that comprises at least (E) an organopolysiloxane that has at least two hydroxyl groups or hydrolyzable groups, e.g., the alkoxy group, oxime group, acetoxy group, aminoxy group, and so forth, bonded to silicon in each molecule, (F) a silane crosslinking agent that has at least three hydrolyzable groups, e.g., the alkoxy group, oxime group, acetoxy group, aminoxy group, and so forth, bonded to silicon in each molecule, and (G) a condensation reaction catalyst such as an organotin compound, an organotitanium compound, and so forth.

The alkoxy group encompassed by component (E) can be exemplified by methoxy, ethoxy, and methoxyethoxy. The oxime group encompassed by component (E) can be exemplified by the dimethyl ketoxime group and the methyl ethyl ketoxime group. The other silicon-bonded organic groups in component (E) can be exemplified by monovalent hydrocarbyl groups such as alkyl groups, e.g., methyl, ethyl, propyl, butyl, and so forth; cycloalkyl groups, e.g., cyclopentyl, cyclohexyl, and so forth; vinyl, allyl, butenyl, pentenyl, and hexenyl; aryl groups such as phenyl, tolyl, xylyl, and so forth; aralkyl groups such as benzyl, phenethyl, 3-phenylpropyl, and so forth; and halogenated alkyl groups such as 3-chloropropyl, 3,3,3-trifluoropropyl, and so forth. The molecular structure of component (E) can be exemplified by straight chain, cyclic, network or mesh, and partially branched straight chain. Straight chain and partially branched straight chain are preferred for forming elastomeric crosslinked silicone particles. The viscosity of component (E) at 25° C. is not limited, but preferably is in the range from 20 to 100,000 mPa·s and particularly preferably is in the range from 20 to 10,000 mPa·s.

The alkoxy and oxime groups encompassed by component (F) can be exemplified by the same groups as given above. Component (F) can be exemplified by methyltrimethoxysilane, vinyltrimethoxysilane, methyltrioximesilane, and vinyltrioximesilane. Component (F) is incorporated in the composition under consideration in an amount sufficient to bring about the crosslinking of this composition, but its quantity of incorporation is not otherwise limited. In specific terms, component (F) is preferably incorporated in an amount within the range from 0.3 to 200 weight parts per 100 weight parts component (E).

Component (G) is a condensation reaction catalyst for the purpose of accelerating or promoting the crosslinking reaction in the composition under consideration and can be specifically exemplified by dibutyltin dilaurate, dibutyltin diacetate, tin octenoate, dibutyltin dioctate, tin laurate, tetrabutyl titanate, tetrapropyl titanate, and dibutoxybis(ethyl acetoacetato)titanium. Component (G) is incorporated in the composition under consideration in an amount sufficient to accelerate or promote the crosslinking reaction in the composition under consideration, but its quantity of incorporation is not otherwise limited. In specific terms, component (G) is incorporated preferably in the range from 0.01 to 5 weight parts per 100 weight parts component (E) and particularly preferably in the range from 0.05 to 2 weight parts per 100 weight parts component (E).

A filler can be incorporated as an optional component in the production method of the present invention in order to adjust the fluidity of the crosslinkable silicone composition and/or to improve the mechanical strength of the resulting crosslinked silicone particles. This filler can be exemplified by reinforcing fillers such as precipitated silica, fumed silica, calcined silica, fumed titanium oxide, and so forth; by non-reinforcing fillers such as quartz powder, diatomaceous earth, aluminosilicates, iron oxide, zinc oxide, calcium carbonate, and so forth; and by the preceding fillers after surface treatment with an organosilicon compound such as hexamethylsilazane, trimethylchlorosilane, polydimethylsiloxane, polymethylhydrogensiloxane, and so forth.

The alkyl-modified silicone oil must be incorporated in the composition under consideration in a quantity that exceeds the quantity of the alkyl-modified silicone oil that can be retained in the crosslinked product from the crosslinkable silicone composition, i.e., the alkyl-modified silicone oil must be incorporated in a quantity that exceeds the quantity of the alkyl-modified silicone oil that this crosslinked product can contain. The amount that can be retained will vary as a function of the particular crosslinkable silicone composition+alkyl-modified silicone oil combination, but as a general matter the alkyl-modified silicone oil is incorporated preferably in the range from 200 to 5,000 weight parts and particularly preferably in the range from 250 to 2,000 weight parts, in each case per 100 weight parts of the crosslinkable silicone composition.

The production method under consideration is characterized by dispersing the alkyl-modified silicone oil-containing crosslinkable silicone composition in water and thereafter bringing about the crosslinking reaction in the crosslinkable silicone composition. The method of dispersing this crosslinkable silicone composition in water can be exemplified by dispersing this composition in the water using a device such as a homomixer, paddle mixer, Henschel mixer, Homo Disper, colloid mill, propeller stirrer, homogenizer, inline continuous emulsifier, ultrasound emulsifier, vacuum kneader/mixer, and so forth.

There is no limitation on the quantity of water used in the production method under consideration, but the water is preferably used within the range from 5 to 99 weight % of the emulsion as a whole and is particularly preferably used within the range from 10 to 80 weight % of the emulsion as a whole.

A nonionic surfactant, e.g., a polyoxyalkylene alkyl ether, polyoxyalkylene alkylphenol, polyoxyalkylene alkyl ester, polyoxyalkylene sorbitan ester, polyethylene glycol, polypropylene glycol, diethylene glycol, ethylene oxide adduct on trimethylnonanol, and so forth; an anionic surfactant, e.g., hexylbenzenesulfonic acid, octylbenzenesulfonic acid, decylbenzenesulfonic acid, dodecylbenzenesulfonic acid, cetylbenzenesulfonic acid, myristylbenzenesulfonic acid, and their sodium salts and so forth; or a cationic surfactant, e.g., octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, beef tallow trimethylammonium hydroxide, cocotrimethylammonium hydroxide, and so forth, is preferably used in order to bring about a highly stable dispersion of the crosslinkable silicone composition in the water, and the use of a nonionic surfactant is particularly preferred. This surfactant is used preferably at from 0.1 to 20 weight parts and particularly preferably at from 0.5 to 10 weight parts, in each case per 100 weight parts of the crosslinkable silicone composition containing the non-crosslinking alkyl-modified silicone oil. A thickener such as 2-phenoxyethanol, carboxymethyl cellulose, xanthan gum, and so forth, may also be incorporated in order to improve the stability of the emulsion.

The average particle size of the water-dispersed crosslinkable silicone composition in the production method under consideration must be in the range from 0.1 to 500 μm and is preferably in the range from 0.2 to 500 μm, more preferably in the range from 0.5 to 500 μm, and particularly preferably in the range from 0.5 to 200 μm. The reasons for this are as follows: it is quite difficult to produce an emulsion in which the average particle size of the water-dispersed crosslinkable silicone composition is below the lower limit on the indicated range, while an emulsion that exceeds the upper limit on the indicated range has a reduced stability.

The crosslinking reaction in the water-dispersed crosslinkable silicone composition can be brought about by heating the thusly produced emulsion of the crosslinkable silicone composition, or by allowing this emulsion to stand at room temperature, or by exposing this emulsion to high energy radiation.

The silicone oil composition of the present invention is described in detail in the following.

The silicone oil composition of the present invention is characteristically provided by removing the water from the silicone oil emulsion containing crosslinked silicone particles in water-dispersed alkyl-modified silicone oil droplets. This silicone oil emulsion is a silicone oil emulsion produced as described in the preceding.

There are no limitations on the method of producing the silicone oil composition, and it can be produced by removing the water using a means such as subjecting the previously described silicone oil emulsion to air drying, drying in a hot air current, vacuum drying, drying with the application of heat, and so forth. The crosslinked silicone particles are uniformly dispersed in the alkyl-modified silicone oil in this silicone oil composition, and the state of this silicone oil composition can be exemplified by liquid, cream, paste, and grease.

The silicone oil emulsion of the present invention and the silicone oil composition of the present invention are well suited for application as a cosmetic material or as an ingredient for a cosmetic material. The type of cosmetic material here can be exemplified by cleansing cosmetics such as soaps, body shampoos, facial cleansing creams, and so forth; basic cosmetics such as face lotions, creams•milky lotions, packs, and so forth; base make-up cosmetics such as facial powders, foundations, and so forth; facial cosmetics such as lipsticks, blushes, eye shadows, eye liners, mascaras, and so forth; make-up cosmetics such as nail polishes and so forth; hair cosmetics such as shampoos, hair rinses, hair conditioners, hair treatments, set lotions, blow styling lotions, hair sprays, foam styling agents, gel styling agents, hair liquids, hair tonics, hair creams, hair growth agents, hair restoration agents, hair dyes, hair styling agents, and so forth; aromatic cosmetics such as perfumes, eau de colognes, and so forth; toothpastes; bath agents; and specialty cosmetics such as depilatories, shaving lotions, antiperspirants•deodorants, and sunscreens. Skin cosmetics such as basic cosmetics and make-up cosmetics as well as hair cosmetics are preferred examples. These cosmetics can be formulated as, for example, water-based liquids, oil-based liquids, emulsions, creams, foams, semi-solids, solids, and powders. These cosmetic products may also be used as sprays.

The following, for example, may be incorporated as cosmetic ingredients when a cosmetic material is produced using this silicone oil emulsion or silicone oil composition: waxes such as carnauba wax, candelilla wax, Rhus succedanea fruit wax, spermaceti, jojoba wax, montan wax, beeswax, and so forth; fats and oils such as liquid paraffin, isoparaffin, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cacao oil, jojoba oil, sesame oil, safflower oil, soy oil, camellia oil, squalane, persic oil, castor oil, mink oil, cottonseed oil, coconut oil, egg yolk oil, lard, and so forth; glycol ester oils such as polypropylene glycol monooleate, neopentyl glycol 2-ethylhexanoate, and so forth; polyhydric alcohol ester oils such as triisostearin, cocofatty acid triglycerides, and so forth; polyoxyalkylene ether oils such as polyoxyethylene lauryl ether, polyoxypropylene cetyl ether; and so forth; and silicone oils such as dimethylpolysiloxane, methylphenylpolysiloxane, octamethyltetracyclosiloxane, decamethylcyclopentasiloxane, polyether-modified silicone oil, amino-modified silicone oils, and so forth.

Other optional cosmetic ingredients can be exemplified by humectants such as glycerol, propylene glycol, 1,3-butylene glycol, polyethylene glycol, sodium d,l-pyrrolidonecarboxylate, sodium lactate, sorbitol, sodium hyaluronate, and so forth; surfactants such as anionic surfactants, e.g., higher fatty acid soaps, higher alcohol sulfate ester salts, N-acylglutamate salts, phosphate esters, and so forth, cationic surfactants, amphoteric surfactants, e.g., betaine types, amino acid types, imidazoline types, lecithin types, and so forth, and nonionic surfactants such as polyhydric alcohol esters, ethylene oxide condensates, and so forth; pigments such as colored pigments, e.g., iron oxide and so forth, white pigments, e.g., zinc oxide, titanium oxide, zirconium oxide, and so forth, and extender pigments such as mica, talc, sericite, and so forth; thickeners such as carrageenan, alginic acid, gum arabic, tragacanth, pectin, starch, xanthan gum, guar gum, carboxymethyl cellulose, carboxyvinyl polymers, polyvinyl alcohol, polyvinylpyrrolidone, hydroxyethyl cellulose, polyoxyethylene glycol distearate, sodium polyalginate, polyethylene glycol, and so forth; ultraviolet absorbers such as benzophenone derivatives such as 2-hydroxy-4-methoxybenzophenone and so forth, benzotriazole derivatives such as 2-(2'-hydroxy-5'-methylphenyl)benzotriazole and so forth, and cinnamate esters; anti-inflammatories such as potassium glycyrrhizate, tocopherol acetate, and so forth; preservatives such as methylparaben, butylparaben, and so forth; antimicrobials such as triclosan, trichlorocarban, and so forth; and antioxidants such as BHA, BHT, γ-oryzanol, and so forth.

In particular, the following, for example, can also be incorporated as cosmetic ingredients when the cosmetic takes the form of a hair cosmetic: surfactants such as nonionic surfactants, e.g., glycerol fatty acid esters such as glycerol monostearate, sorbitan fatty acid esters such as sorbitan monopalmitate, polyoxyethylene alkyl ethers such as polyoxyethylene cetyl ether, polyoxyethylene fatty acid esters such as polyoxyethylene stearate and polyoxyethylene sorbitan monolaurate, as well as polyoxyethylene alkylphenyl ethers, polyoxyethylene castor oil, polyoxyethylene hardened castor oil, and the alkylolamides of fatty acids, cationic surfactants such as monoalkyltrimethylammonium salts, e.g., stearyltrimethylammonium chloride and behenyltrimethylammonium chloride, and dialkyldimethylammonium salts, e.g., distearyldimethylammonium chloride and dibehenyldimethylammonium chloride, and amphoteric surfactants; film-forming agents such as the polymers of (meth)acrylic-type radically polymerizable monomers and their copolymers with silicone compounds, poly(N-acylalkyleneimine), poly(N-methylpyrrolidone), silicone resins modified by a fluorine-containing organic group and/or the amino group, and unmodified silicone resins; anti-dandruff agents such as sulfur, selenium sulfide, zinc pyrithione, octopirox, zinc pyridium-1-thiol-N-oxide, salicylic acid, 2,4,4'-trichloro-2'-hydroxydiphenyl ether, 1-hydroxy-2-pyridone compounds, and so forth; tactile feel improvers such as squalane, lanolin, perfluoropolyether, cationic polymers, and so forth; antifreezes such as ethanol, isopropyl alcohol, 1,3-butylene glycol, ethylene glycol, propylene glycol, glycerol, and so forth; chelating agents such as ethylenediaminetetraacetic acid, citric acid, ethane-1-hydroxy-1,1-diphosphonic acid, and salts of the preceding; colorants such as pearlescent agents, pigments, dyes, and so forth; vitamins; hair restoration agents; hormones; fragrances; pH modifiers; propellants; and the components described in the Encyclopedia of Shampoo Ingredients (Micelle Press, 1985).

There is no limitation on the quantity of incorporation of the silicone oil emulsion or silicone oil composition when this emulsion or composition is used to produce a cosmetic material, but the emulsion or composition is preferably used at 0.1 to 99.9 weight % in the cosmetic material and particularly preferably at 0.5 to 99 weight % in the cosmetic material, in each case calculated on the basis of the components other than water, i.e., calculated on the basis of the solids fraction. The reasons for this are as follows: when the quantity of incorporation of the silicone oil emulsion or silicone oil composition exceeds the upper limit on the previously indicated range, the effect as a cosmetic material tends to be lost; on the other hand, obtaining improvements in, for example, the use sensation, tends to be problematic at below the lower limit on the previously indicated range.

EXAMPLES

The silicone oil emulsion of the present invention, the method according to the present invention of producing this silicone oil emulsion, and the silicone oil composition of the present invention are described in detail using examples. The viscosity values given in the examples were measured at 25° C. The average particle size and stability of the silicone oil emulsions, the average particle size and dispersibility of the crosslinked silicone particles, and the viscoelasticity of the silicone oil compositions were determined as follows.

[Average Particle Size of the Silicone Oil Emulsion]

The silicone oil emulsion was measured using an LA-750 laser diffraction particle size distribution analyzer from Horiba, Ltd., and the obtained median diameter, which was the particle diameter corresponding to 50% in the cumulative distribution, was used as the average particle size.

[Stability of the Silicone Oil Emulsion]

180 mL of the silicone oil emulsion was sealed in a 225-mL glass bottle having a depth of 105 mm and a mouth diameter of 50 mm and was then held at quiescence for 1 week at room temperature. After standing, the thickness of the aqueous layer that had separated from the emulsion was measured.

[Average Particle Size of the Crosslinked Silicone Particles]

The silicone oil emulsion was air dried on a glass plate, and a sample was prepared by collecting the crosslinked silicone particles under a stereomicroscope. This sample was observed with an electron microscope, and the average particle size was determined from 10 particle diameters.

[Dispersibility of the Crosslinked Silicone Particles]

The silicone oil emulsion was air dried on a glass plate and the shape of the crosslinked silicone particles, their aggregation status, and their distribution were observed with a stereomicroscope. A score of "+" was rendered when all of the crosslinked silicone particles were dispersed as primary particles; a score of "×" was rendered when aggregated particles of several hundred micrometers were present or when primary particles of 500 μm or more were present; while a state intermediate between the preceding was scored with a "Δ".

[Viscoelasticity of the Silicone Oil Composition]

The strage modulus G' (Pa), the loss modulus G" (Pa), and the loss tangent tan δ were measured on the silicone oil composition using an ARES viscoelasticity analyzer from Rheometric Scientific. The measurement conditions were as follows: room temperature, 25 mm parallel plates, gap=0.5 to 0.6 mm, strain=10%, oscillation rate=0.01 to 50 Hz.

Practical Example 1

The following were mixed to produce a crosslinkable silicone composition: 15.3 weight parts of a dimethylpolysiloxane endblocked by the dimethylvinylsiloxy group at both molecular chain terminals and having a viscosity of 400 mPa·s and a vinyl content of 0.48 weight %, 4.70 weight parts of a dimethylsiloxane•methylhydrogensiloxane copolymer endblocked by the trimethylsiloxy group at both molecular chain terminals and having a viscosity of 75 mPa·s and a silicon-bonded hydrogen content of 0.05 weight %, and 80 weight parts of an alkyl-modified silicone oil having the following average formula

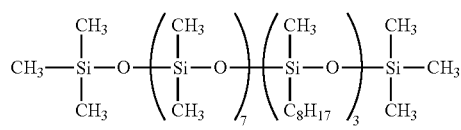

and a viscosity of 30 mPa·s.

An aqueous solution was prepared by dissolving 1.6 weight parts of a polyoxyethylene alkyl ether having an HLB of 14.5 and 1.6 weight parts 2-phenoxyethanol in 96.8 weight parts pure water, and 29.5 weight parts of this previously prepared aqueous solution was added to the composition prepared as above. After emulsification using a colloid mill, an additional 27.6 weight parts pure water was added to give a water-based emulsion of the crosslinkable silicone composition.

To this emulsion was added a water-based emulsion of a platinum catalyst in which the main component was a 1,3-divinyl-1,1,3,3-tetramethyldisiloxane complex of platinum and mixing to uniformity was performed. This water-based platinum catalyst emulsion had an average platinum catalyst particle size of 0.05 μm and a platinum metal concentration of 0.05 weight %, and it was added in an amount that provided 10 weight-ppm platinum metal with reference to the crosslinkable silicone composition in the water-based emulsion of the crosslinkable silicone composition.

The crosslinkable silicone composition was crosslinked via the hydrosilylation reaction by holding the water-based emulsion of the crosslinkable silicone composition for 1 day at 50° C.; this produced an alkyl-modified silicone oil emulsion that contained silicone rubber particles in alkyl-modified silicone oil droplets that were dispersed in the water. The properties of this emulsion are given in Table 1. A portion of this emulsion was collected and hair was immersed therein followed by drying. The hair resisted tangling, and a silky smooth feel was imparted to the hair.

This emulsion was then introduced into a Model HV-030 Vacuum Mixer combination mixer from the STM Co., Ltd. While stirring at an anchor mixer rotation rate of 90 rpm and a disperser rotation rate of 1,000 rpm, the water was removed by reducing the pressure while raising the temperature to 75 to 85° C. over 1 to 2 hours and holding for 1 hour at 50 mmHg or below. This was followed by cooling to room temperature to obtain a liquid alkyl-modified silicone oil composition. When this composition was observed with a stereomicroscope, the silicone rubber particles were found to be uniformly dispersed in the alkyl-modified silicone oil and to have a spherical shape. The properties of this composition are given in Table 1. A portion of this composition was collected and spread on the back of the hand with a finger: it spread very smoothly and demonstrated a suitable spreadability. In addition, a lustrous and water-repellent film could be formed on the back of the hand.

Practical Example 2

The following were mixed to produce a crosslinkable silicone composition: 18.41 weight parts of a dimethylpolysiloxane•methylvinylsiloxane copolymer endblocked by the dimethylvinylsiloxy group at both molecular chain terminals and having a viscosity of 400 mPa·s and a vinyl content of 1.18 weight %, 1.59 weight parts of a dimethylsiloxane•methylhydrogensiloxane copolymer endblocked by the trimethylsiloxy group at both molecular chain terminals and having a viscosity of 50 mPa·s and a silicon-bonded hydrogen content of 0.43 weight %, and 80 weight parts of an alkyl-modified silicone oil having the following average formula

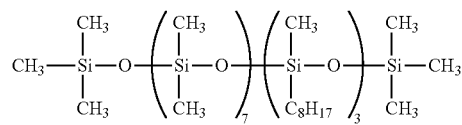

and a viscosity of 30 mPa·s.

The water-based emulsion of this composition was prepared as in Example 1 and crosslinking via the hydrosilylation reaction was carried out also as in Example 1 to produce an alkyl-modified silicone oil emulsion that contained silicone rubber particles in alkyl-modified silicone oil droplets that were dispersed in the water. The properties of this emulsion are given in Table 1. A portion of this emulsion was collected and hair was immersed therein followed by drying. The hair resisted tangling, and a silky smooth feel was imparted to the hair.

The water was then removed from this emulsion using the procedure described in Example 1 to produce an alkyl-modified silicone oil composition paste. When this alkyl-modified silicone oil composition was observed with a stereomicroscope, the silicone rubber particles were found to be uniformly dispersed in the alkyl-modified silicone oil and to have a spherical shape. The properties of this composition are given in Table 1. A portion of this composition was collected and spread on the back of the hand with a finger: it spread very smoothly and demonstrated a suitable spreadability. In addition, a lustrous and water-repellent film could be formed on the back of the hand.

Practical Example 3

The following were mixed to uniformity to produce a crosslinkable silicone composition: 9.05 weight parts of a dimethylpolysiloxane endblocked by the hydroxyl group at both molecular chain terminals and having a viscosity of 40 mPa·s and a hydroxyl group content of 3.8 weight %, 0.95 weight part of a methylhydrogenpolysiloxane endblocked by the trimethylsiloxy group at both molecular chain terminals and having a viscosity of 20 mPa·s and a silicon-bonded hydrogen content of 1.56 weight %, 90 weight parts of an alkyl-modified silicone oil having the following average formula

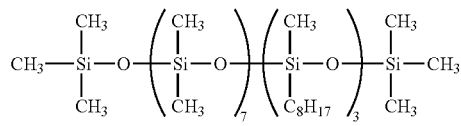

and a viscosity of 30 mPa·s, and 0.10 weight part tin dioctylate.

An aqueous solution was prepared by dissolving 1.6 weight parts of a polyoxyethylene alkyl ether having an HLB of 14.5 and 1.6 weight parts 2-phenoxyethanol in 96.8 weight parts pure water, and 29.5 weight parts of this previously prepared aqueous solution was added to the composition prepared as above. After emulsification using a colloid mill, an additional 29.1 weight parts pure water was added to give a water-based emulsion of the crosslinkable silicone composition.

The crosslinkable silicone composition was crosslinked via a condensation reaction by holding the water-based emulsion of the crosslinkable silicone composition for 1 week at room temperature; this produced an alkyl-modified silicone oil emulsion that contained silicone rubber particles in alkyl-modified silicone oil droplets that were dispersed in the water. The properties of this emulsion are given in Table 1. A portion of this emulsion was collected and hair was immersed therein followed by drying. The hair resisted tangling, and a silky smooth feel was imparted to the hair.

The water was then removed from this emulsion using the procedure in Example 1 to produce a liquid alkyl-modified silicone oil composition. When this alkyl-modified silicone oil composition was observed with a stereomicroscope, the silicone rubber particles were found to be uniformly dispersed in the alkyl-modified silicone oil and to have a spherical shape. The properties of this composition are given in Table 1. A portion of this composition was collected and spread on the back of the hand with a finger: it spread very smoothly and demonstrated a suitable spreadability. In addition, a lustrous and water-repellent film could be formed on the back of the hand.

Practical Example 4

The following were mixed to produce a crosslinkable silicone composition: 14.22 weight parts of a dimethylpolysiloxane endblocked by the dimethylvinylsiloxy group at both molecular chain terminals and having a viscosity of 400 mPa·s and a vinyl content of 0.48 weight %, 0.78 weight part of a dimethylsiloxane•methylhydrogensiloxane copolymer endblocked by the trimethylsiloxy group at both molecular chain terminals and having a viscosity of 45 mPa·s and a silicon-bonded hydrogen content of 0.31 weight %, and 85 weight parts of an alkyl-modified silicone oil having the following average formula

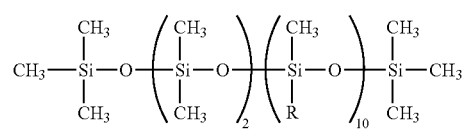

and a viscosity of 150 mPa·s wherein R in the formula was a mixture of —$C_2H_{25}$ and —$C_{14}H_{29}$.

The water-based emulsion of this composition was prepared as in Example 1 and crosslinking via the hydrosilylation reaction was carried out also as in Example 1 to produce an alkyl-modified silicone oil emulsion that contained silicone rubber particles in alkyl-modified silicone oil droplets that were dispersed in the water. The properties of this emulsion are given in Table 1. A portion of this emulsion was collected and hair was immersed therein followed by drying. The hair resisted tangling, and a silky smooth feel was imparted to the hair.

The water was then removed from this emulsion using the procedure described in Example 1 to produce an alkyl-modified silicone oil composition that was a somewhat viscous liquid. When this alkyl-modified silicone oil composition was observed with a stereomicroscope, the silicone rubber particles were found to be uniformly dispersed in the alkyl-modified silicone oil and to have a spherical shape. The properties of this composition are given in Table 1. A portion of this composition was collected and spread on the back of the hand with a finger: it spread very smoothly and demonstrated a suitable spreadability. In addition, a lustrous and water-repellent film could be formed on the back of the hand.

Comparative Example 1

A silicone oil emulsion containing silicone rubber particles and a silicone oil composition paste containing silicone rubber particles were produced as in Example 1, but in this case replacing the alkyl-modified silicone oil used in Example 1 with the same amount of a dimethylpolysiloxane endblocked by the trimethylsiloxy group at both molecular chain terminals and having a viscosity of 6 mPa·s.

The properties of this emulsion and silicone oil composition are given in Table 1. In addition, a portion of the emulsion was collected and hair was immersed therein followed by drying. The ability of the hair to resist tangling was not improved, and a silky smooth feel could not be imparted to the hair. A portion of this composition was collected and spread on the back of the hand with a finger: it tended to spread out too much and its spreadability was thus unsuitable. In addition, a dull water-repellent film was formed on the back of the hand.

Comparative Example 2

A silicone oil emulsion containing silicone rubber particles and a silicone oil composition paste containing silicone rubber particles were produced as in Example 2, but in this case replacing the alkyl-modified silicone oil used in Example 2 with the same amount of a dimethylpolysiloxane endblocked by the trimethylsiloxy group at both molecular chain terminals and having a viscosity of 6 mPa·s. The properties of this emulsion and silicone oil composition are given in Table 1.

Comparative Example 3

The following were mixed to produce a crosslinkable silicone composition: 92.10 weight parts of a dimethylpolysiloxane•methylvinylsiloxane copolymer endblocked by the dimethylvinylsiloxy group at both molecular chain terminals and having a viscosity of 400 mPa·s and a vinyl content of 1.18 weight % and 7.90 weight parts of a dimethylsiloxane•methylhydrogensiloxane copolymer endblocked by the trimethylsiloxy group at both molecular chain terminals and having a viscosity of 50 mPa·s and a silicon-bonded hydrogen content of 0.43 weight %.

An aqueous solution was prepared by dissolving 1.6 weight parts of a polyoxyethylene alkyl ether having an HLB of 14.5 and 1.6 weight parts 2-phenoxyethanol in 96.8 weight parts pure water, and 29.5 weight parts of this previously prepared aqueous solution was added to the composition prepared as above. After emulsification using a colloid mill, an additional 27.6 weight parts pure water was added to give a water-based emulsion of the crosslinkable silicone composition.

To this emulsion was added a water-based emulsion of a platinum catalyst in which the main component was a 1,3-divinyl-1,1,3,3-tetramethyldisiloxane complex of platinum and mixing to uniformity was performed. This water-based platinum catalyst emulsion had an average platinum catalyst particle size of 0.05 μm and a platinum metal concentration of 0.05 weight %, and it was added in an amount that provided 10 weight-ppm platinum metal with reference to the crosslinkable silicone composition in the water-based emulsion of the crosslinkable silicone composition.

The crosslinkable silicone composition was crosslinked via the hydrosilylation reaction by holding the water-based emulsion of the crosslinkable silicone composition for 1 day at 50° C.; this produced a water-based suspension of silicone rubber particles. This suspension was air dried for 1 week at room temperature to produce silicone rubber particles.

20 weight parts of these silicone rubber particles and 80 weight parts of an alkyl-modified silicone oil having the following average formula

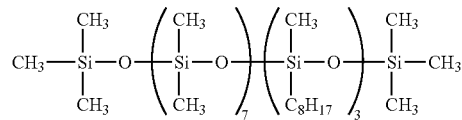

and a viscosity of 30 mPa·s were mixed for 10 minutes at 300 rpm using a blade-type stirrer (3:1 motor). The mixture contained aggregated particles that could be felt with the fingers and a uniform composition was thus not obtained. When observation was performed after 1 week, the silicone rubber particles were found to have undergone sedimentation.

Comparative Example 4

A silicone oil emulsion containing silicone rubber particles and a silicone oil composition paste containing silicone rubber particles were produced as in Example 4, but in this case replacing the alkyl-modified silicone oil used in Example 4 with the same amount of a dimethylpolysiloxane endblocked by the trimethylsiloxy group at both molecular chain terminals and having a viscosity of 6 mPa·s. The properties of this emulsion and silicone oil composition are given in Table 1.

TABLE 1

| | | classification | | | | | | |
| --- | --- | --- | --- | --- | --- | --- | --- | --- |
| | | Practical Example | | | | Comparative Example | | |
| item | | 1 | 2 | 3 | 4 | 1 | 2 | 4 |
| silicone oil emulsion | | | | | | | | |
| average particle size (μm) | | 2.8 | 2.7 | 2.1 | 2.5 | 2.6 | 2.4 | 2.7 |
| stability | | + | + | + | + | + | + | + |
| crosslinked silicone particles | | | | | | | | |
| average particle size (μm) | | 2.6 | 2.2 | 1.8 | 2.2 | 2.4 | 2.3 | 2.4 |
| dispersibility | | + | + | + | + | + | + | + |
| viscoelasticity of the silicone oil composition | | | | | | | | |
| G' | 0.1 Hz | 4.5 | 372 | 21 | 41.9 | 603 | 787 | 874 |
| | 1.0 Hz | 9.0 | 635 | 25 | 62.6 | 732 | 2378 | 956 |
| G" | 0.1 Hz | 4.5 | 151 | 6.3 | 31.9 | 86 | 1356 | 74.7 |
| | 1.0 Hz | 12.7 | 244 | 9.3 | 66.1 | 176 | 2044 | 149 |
| tan δ | 0.1 Hz | 1.0 | 0.41 | 0.30 | 0.8 | 0.14 | 1.7 | 0.09 |
| | 1.0 Hz | 1.4 | 0.38 | 0.36 | 1.1 | 0.24 | 0.86 | 0.15 |

Practical Example 5

The following were mixed to produce a crosslinkable silicone composition: 15.74 weight parts of a dimethylsiloxane•methylvinylsiloxane copolymer endblocked by the dimethylvinylsiloxy group at both molecular chain terminals and having a viscosity of 400 mPa·s and a vinyl content of 1.18 weight %, 3.02 weight parts of a dimethylsiloxane•methylhydrogensiloxane copolymer endblocked by the trimethylsiloxy group at both molecular chain terminals and having a viscosity of 50 mPa·s and a silicon-bonded hydrogen content of 0.43 weight %, 1.22 weight parts 1-docene, and 80 weight parts of an alkyl-modified silicone oil having the following average formula

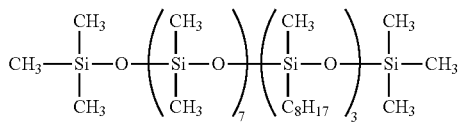

and a viscosity of 30 mPa·s.

An aqueous solution was prepared by dissolving 1.6 weight parts of a polyoxyethylene alkyl ether having an HLB of 14.5 and 1.6 weight parts 2-phenoxyethanol in 96.8 weight parts pure water, and 29.5 weight parts of this previously prepared aqueous solution was added to the composition prepared as above. After emulsification using a colloid mill, an additional 27.6 weight parts pure water was added to give a water-based emulsion of the crosslinkable silicone composition.

To this emulsion was added a water-based emulsion of a platinum catalyst in which the main component was a 1,3-divinyl-1,1,3,3-tetramethyldisiloxane complex of platinum and mixing to uniformity was performed. This water-based platinum catalyst emulsion had an average platinum catalyst particle size of 0.05 μm and a platinum metal concentration of 0.05 weight %, and it was added in an amount that provided 10 weight-ppm platinum metal with reference to the crosslinkable silicone composition in the water-based emulsion of the crosslinkable silicone composition.

The crosslinkable silicone composition was crosslinked via the hydrosilylation reaction by holding the water-based emulsion of the crosslinkable silicone composition for 1 day at 50° C.; this produced an alkyl-modified silicone oil emulsion that contained silicone rubber particles in alkyl-modified silicone oil droplets that were dispersed in the water. The properties of this emulsion are given in Table 2. A portion of this emulsion was collected and hair was immersed therein followed by drying. The hair resisted tangling, and a silky smooth feel was imparted to the hair.

This emulsion was then introduced into a Model HV-030 Vacuum Mixer combination mixer from the STM Co., Ltd. While stirring at an anchor mixer rotation rate of 90 rpm and a disperser rotation rate of 1,000 rpm, the water was removed by reducing the pressure while raising the temperature to 75 to 85° C. over 1 to 2 hours and holding for 1 hour at 50 mmHg or below. This was followed by cooling to room temperature to obtain a liquid alkyl-modified silicone oil composition. When this alkyl-modified silicone oil composition was observed with a stereomicroscope, the silicone rubber particles were found to be uniformly dispersed in the alkyl-modified silicone oil and to have a spherical shape. The properties of this composition are given in Table 2. A portion of this composition was collected and spread on the back of the hand with a finger: it spread very smoothly and demonstrated a suitable spreadability. In addition, a lustrous and water-repellent film could be formed on the back of the hand.

Practical Example 6

The following were mixed to produce a crosslinkable silicone composition: 31.49 weight parts of a dimethylpolysiloxane•methylvinylsiloxane copolymer endblocked by the dimethylvinylsiloxy group at both molecular chain terminals and having a viscosity of 400 mPa·s and a vinyl content of 1.18 weight %, 6.08 weight parts of a dimethylsiloxane•methylhydrogensiloxane copolymer endblocked by the trimethylsiloxy group at both molecular chain terminals and having a viscosity of 50 mPa·s and a silicon-bonded hydrogen content of 0.43 weight %, 2.43 weight parts 1-dodecene, and 60 weight parts of an alkyl-modified silicone oil having the following average formula

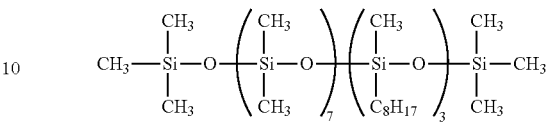

and a viscosity of 30 mPa·s.

The water-based emulsion of this composition was prepared as in Example 1 and crosslinking via the hydrosilylation reaction was carried out also as in Example 1 to produce an alkyl-modified silicone oil emulsion that contained silicone rubber particles in alkyl-modified silicone oil droplets that were dispersed in the water. The properties of this emulsion are given in Table 2. A portion of this emulsion was collected and hair was immersed therein followed by drying. The hair resisted tangling, and a silky smooth feel was imparted to the hair.

The water was then removed from this emulsion using the procedure described in Example 1 to produce an alkyl-modified silicone oil composition paste. When this alkyl-modified silicone oil composition was observed with a stereomicroscope, the silicone rubber particles were found to be uniformly dispersed in the alkyl-modified silicone oil and to have a spherical shape. The properties of this composition are given in Table 2. A portion of this composition was collected and spread on the back of the hand with a finger: it spread very smoothly and demonstrated a suitable spreadability. In addition, a lustrous and water-repellent film could be formed on the back of the hand.

Comparative Example 5

A silicone oil emulsion containing silicone rubber particles and a silicone oil composition crumb containing silicone rubber particles were produced as in Example 6, but in this case replacing the alkyl-modified silicone oil used in Example 6 with the same amount of a dimethylpolysiloxane endblocked by the trimethylsiloxy group at both molecular chain terminals and having a viscosity of 6 mPa·s.

The properties of this emulsion and silicone oil composition are given in Table 2. In addition, a portion of the emulsion was collected and hair was immersed therein followed by drying. The ability of the hair to resist tangling was not improved, and a silky smooth feel could not be imparted to the hair. A portion of this composition was collected and spread on the back of the hand with a finger: it tended to spread out too much and its spreadability was thus unsuitable. In addition, a dull water-repellent film was formed on the back of the hand.

Comparative Example 6

A silicone oil emulsion containing silicone rubber particles and a silicone oil composition crumb containing silicone rubber particles were produced as in Example 7, but in this case replacing the alkyl-modified silicone oil used in Example 7 with the same amount of a dimethylpolysiloxane endblocked by the trimethylsiloxy group at both molecular chain terminals and having a viscosity of 6 mPa·s.

The properties of this emulsion and silicone oil composition are given in Table 2. In addition, a portion of the emulsion was collected and hair was immersed therein followed by drying. The ability of the hair to resist tangling was not improved, and a silky smooth feel could not be imparted to the hair.

Comparative Example 7

The following were mixed to produce a crosslinkable silicone composition: 78.71 weight parts of a dimethylpolysiloxane•methylvinylsiloxane copolymer endblocked by the dimethylvinylsiloxy group at both molecular chain terminals and having a viscosity of 400 mPa·s and a vinyl content of 1.18 weight %, 15.21 weight parts of a dimethylsiloxane•methylhydrogensiloxane copolymer endblocked by the trimethylsiloxy group at both molecular chain terminals and having a viscosity of 50 mPa·s and a silicon-bonded hydrogen content of 0.43 weight %, and 6.08 weight parts 1-dodecene.

An aqueous solution was prepared by dissolving 1.6 weight parts of a polyoxyethylene alkyl ether having an HLB of 14.5 and 1.6 weight parts 2-phenoxyethanol in 96.8 weight parts pure water, and 29.5 weight parts of this previously prepared aqueous solution was added to the composition prepared as above. After emulsification using a colloid mill, an additional 27.6 weight parts pure water was added to give a water-based emulsion of the crosslinkable silicone composition.

To this emulsion was added a water-based emulsion of a platinum catalyst in which the main component was a 1,3-divinyl-1,1,3,3-tetramethyldisiloxane complex of platinum and mixing to uniformity was performed. This water-based platinum catalyst emulsion had an average platinum catalyst particle size of 0.05 μm and a platinum metal concentration of 0.05 weight %, and it was added in an amount that provided 10 weight-ppm platinum metal with reference to the crosslinkable silicone composition in the water-based emulsion of the crosslinkable silicone composition.

The crosslinkable silicone composition was crosslinked via the hydrosilylation reaction by holding the water-based emulsion of the crosslinkable silicone composition for 1 day at 50° C.; this produced a water-based suspension of silicone rubber particles. This suspension was air dried for 1 week at room temperature to produce silicone rubber particles.

20 weight parts of these silicone rubber particles and 80 weight parts of an alkyl-modified silicone oil having the following average formula

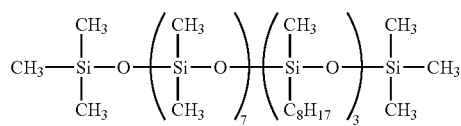

and a viscosity of 30 mPa·s were mixed for 10 minutes at 300 rpm using a blade-type stirrer (3:1 motor). The mixture contained aggregated particles that could be felt with the fingers and a uniform composition was thus not obtained. When observation was performed after 1 week, the silicone rubber particles were found to have undergone sedimentation.

TABLE 2

| item | classification | | | |
|---|---|---|---|---|
| | Practical Example 5 | Practical Example 6 | Comparative Example 5 | Comparative Example 6 |
| silicone oil emulsion | | | | |
| average particle size (μm) | 2.6 | 3.0 | 2.8 | 2.5 |
| stability | + | + | + | + |
| crosslinked silicone particles | | | | |
| average particle size (μm) | 1.8 | 2.7 | 2.4 | 2.3 |
| dispersibility | + | + | + | + |
| viscoelasticity of the silicone oil composition | | | | |
| G' 0.1 Hz | 3.2 | 588 | 1401 | 1130 |
| 1.0 Hz | 6.6 | 1743 | 2721 | 2360 |
| G" 0.1 Hz | 1.1 | 1707 | 1770 | 2282 |
| 1.0 Hz | 4.7 | 3790 | 2451 | 3382 |
| tan δ 0.1 Hz | 0.36 | 2.9 | 1.3 | 2.0 |
| 1.0 Hz | 0.72 | 2.2 | 0.90 | 1.4 |

INDUSTRIAL APPLICABILITY

The silicone oil emulsion of the present invention is well qualified for use as a cosmetic ingredient or a cosmetic material. This emulsion is particularly well qualified for application as a hair cosmetic because it makes hair resistant to tangling and can impart a silky smooth feel to hair. In addition, the removal of the water from this emulsion can produce a silicone oil composition in which crosslinked silicone particles are uniformly dispersed in an alkyl-modified silicone oil. This composition is well qualified for use as a lubricating agent, as an additive for resins and plastics, and as a cosmetic ingredient and cosmetic material. This composition is particularly well qualified for application to skin cosmetics because it can provide a suitable spreadability during application to the skin and post-application can form a lustrous and water-repellent film.

When used as a cosmetic ingredient or cosmetic material, the silicone oil emulsion of the present invention and silicone oil composition of the present invention exhibit an excellent compatibility with organic components such as UV absorbers, vitamins, and so forth. Sedimentation of the crosslinked silicone particles is inhibited in particular when the crosslinked silicone particles have a silicon-bonded alkyl group having at least 4 carbons.

The invention claimed is:

1. A silicone oil emulsion comprising crosslinked silicone particles having an average particle size of 0.05 to 100 μm in silicone oil droplets that are dispersed in water and that have an average particle size of 0.1 to 500 μm wherein the particle size of the crosslinked silicone particles is less than the particle size of the silicone oil droplets, characterized in that the silicone oil is an alkyl-modified silicone oil that has a silicon-bonded alkyl group having at least 4 carbons and is represented by the following average formula

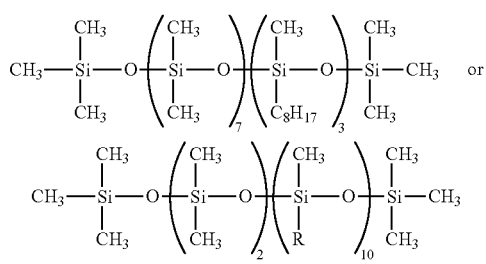

wherein R in the formula is a mixture of —$C_{12}H_{25}$ and —$C_{14}H_{29}$.

2. The silicone oil emulsion according to claim 1, wherein the crosslinked silicone particle also has a silicon-bonded alkyl group having at least 4 carbons.

3. A cosmetic ingredient or a cosmetic material comprising the silicone oil emulsion according to claim 1.

4. A production method of a silicone oil emulsion wherein the emulsion is provided by a crosslinking reaction of a crosslinkable silicone composition containing a non-crosslinking silicone oil in water and the emulsion contains crosslinked silicone particles having an average particle size of 0.05 to 100 μm in silicone oil droplets that are dispersed in the water as particles having an average particle size of 0.1 to 500 μm wherein the particle size of the crosslinked silicone particles is less than the particle size of the silicone oil droplets, the production method of the silicone oil emulsion is characterized in that the silicone oil is an alkyl-modified silicone oil that has a silicon-bonded alkyl group having at least 4 carbons and is represented by the following average formula

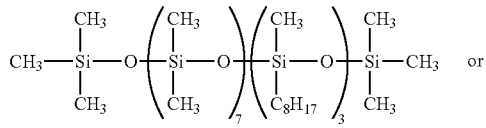

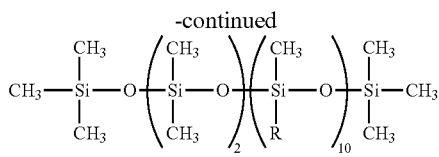

wherein R in the formula is a mixture of —$C_{12}H_{25}$ and —$C_{14}H_{29}$.

5. The production method according to claim 4, wherein the crosslinked silicone particle also has a silicon-bonded alkyl group having at least 4 carbons.

6. A silicone oil composition provided by removing the water from a silicone oil emulsion that contains crosslinked silicone particles having an average particle size of 0.05 to 100 μm in silicone oil droplets that are dispersed in water and that have an average particle size of 0.1 to 500 μm wherein the particle size of the crosslinked silicone particles is less than the particle size of the silicone oil droplets, characterized in that the silicone oil is an alkyl-modified silicone oil that has an at least $C_4$ alkyl group bonded to silicon carbons and is represented by the following average formula

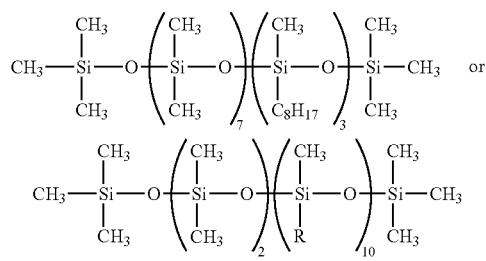

wherein R in the formula is a mixture of —$C_{12}H_{25}$ and —$C_{14}H_{29}$.

7. The silicone oil composition according to claim 6, wherein the crosslinked silicone particle also has a silicon-bonded alkyl group having at least 4 carbons.

8. A cosmetic ingredient or a cosmetic material comprising the silicone oil composition according to claim 6.

* * * * *